(12) United States Patent
Pagliuca et al.

(10) Patent No.: US 7,682,370 B2
(45) Date of Patent: Mar. 23, 2010

(54) SURGICAL TOOL FOR USE IN EXPANDING A CANNULA

(75) Inventors: James J. Pagliuca, Millis, MA (US); John D. Unger, Wrentham, MA (US); James E. Robbins, North Attleboro, MA (US); Thomas W. Davison, Naples, FL (US); Adam Sher, Franklin, MA (US)

(73) Assignee: Zimmer Spine, Inc., Minneapolis, MN (US)

( * ) Notice: Subject to any disclaimer, the term of this patent is extended or adjusted under 35 U.S.C. 154(b) by 1362 days.

(21) Appl. No.: 10/665,754

(22) Filed: Sep. 19, 2003

(65) Prior Publication Data

US 2004/0116954 A1    Jun. 17, 2004

Related U.S. Application Data

(63) Continuation-in-part of application No. 09/906,463, filed on Jul. 16, 2001, now Pat. No. 6,652,553, which is a continuation-in-part of application No. 09/772,605, filed on Jan. 30, 2001, now Pat. No. 6,800,084, which is a continuation-in-part of application No. 09/137,335, filed on Aug. 20, 1998, now Pat. No. 6,187,000.

(51) Int. Cl.
*A61M 29/00* (2006.01)

(52) U.S. Cl. .................... 606/191; 604/104; 604/264

(58) Field of Classification Search ................ 606/191, 606/198, 105, 190; 604/104, 105, 264; 222/460; 600/214, 219, 220, 225, 244
See application file for complete search history.

(56) References Cited

U.S. PATENT DOCUMENTS

| | | |
|---|---|---|
| 1,170,324 A | 2/1916 | Pomerene |
| 3,044,461 A | 7/1962 | Murdock |
| 3,503,398 A | 3/1970 | Fogarty et al. |

(Continued)

FOREIGN PATENT DOCUMENTS

EP    0807415    12/2003

(Continued)

OTHER PUBLICATIONS

Ditsworth, "Endoscopic Transforaminal Lumbar Discectomy and Reconfiguration: A Posterolateral Approach Into the Spinal Canal," Surg. Neurol., 49: 588-598, 1998.

(Continued)

*Primary Examiner*—Michael J Milano
*Assistant Examiner*—Victor X Nguyen
(74) *Attorney, Agent, or Firm*—Crompton, Seager & Tufte, LLC

(57) ABSTRACT

A surgical tool for use in expanding a tubular structure having an inner surface defining a passage through the tubular structure for receiving surgical instruments includes a first leg having a first end engageable with the inner surface of the tubular structure. A second leg has a second end engageable with the inner surface of the tubular structure. The first and second ends are movable away from each other to apply a radially outwardly directed force to the inner surface of the tubular structure and cause expansion of the tubular structure to increase a cross-sectional area of the passage along a portion of the passage.

19 Claims, 11 Drawing Sheets

U.S. PATENT DOCUMENTS

| | | | |
|---|---|---|---|
| 3,789,852 A | 2/1974 | Kim et al. | |
| 4,449,532 A | 5/1984 | Storz | |
| 4,451,256 A | 5/1984 | Weikl et al. | |
| 4,545,374 A | 10/1985 | Jacobson | |
| 4,573,448 A | 3/1986 | Kambin | |
| 4,863,133 A | 9/1989 | Bonnell | |
| 4,899,729 A | 2/1990 | Gill et al. | |
| 4,921,478 A | 5/1990 | Solano et al. | |
| 4,984,564 A | 1/1991 | Yuen | |
| 5,163,949 A | 11/1992 | Bonutti | |
| 5,196,023 A | 3/1993 | Martin | |
| 5,197,971 A | 3/1993 | Bonutti | |
| 5,295,994 A | 3/1994 | Bonutti | |
| 5,312,351 A * | 5/1994 | Gerrone | 604/117 |
| 5,312,417 A | 5/1994 | Wilk | |
| 5,345,927 A | 9/1994 | Bonutti | |
| 5,354,302 A | 10/1994 | Ko | |
| 5,370,647 A | 12/1994 | Graber et al. | |
| 5,370,659 A | 12/1994 | Sakashita | |
| 5,395,317 A | 3/1995 | Kambin | |
| 5,417,203 A | 5/1995 | Tovey et al. | |
| 5,443,479 A | 8/1995 | Bressi, Jr. | |
| 5,454,365 A | 10/1995 | Bonutti | |
| 5,490,819 A | 2/1996 | Nicholas et al. | |
| 5,529,571 A | 6/1996 | Daniel | |
| 5,577,993 A * | 11/1996 | Zhu et al. | 600/204 |
| 5,601,590 A | 2/1997 | Bonutti et al. | |
| 5,667,520 A | 9/1997 | Bonutti | |
| 5,683,349 A * | 11/1997 | Makower et al. | 600/214 |
| 5,690,606 A | 11/1997 | Slotman | |
| 5,707,359 A | 1/1998 | Bufalini | |
| 5,728,113 A * | 3/1998 | Sherts | 606/145 |
| 5,762,629 A | 6/1998 | Kambin | |
| 5,795,289 A | 8/1998 | Wyttenbach | |
| 5,813,978 A * | 9/1998 | Jako | 600/201 |
| 5,851,214 A | 12/1998 | Larsen et al. | |
| 5,865,802 A | 2/1999 | Yoon et al. | |
| 5,902,231 A | 5/1999 | Foley et al. | |
| 5,961,499 A | 10/1999 | Bonutti et al. | |
| 5,976,161 A | 11/1999 | Kirsch et al. | |
| 6,036,638 A * | 3/2000 | Nwawka | 600/186 |
| 6,120,437 A | 9/2000 | Yoon et al. | |
| 6,126,671 A | 10/2000 | Richards et al. | |
| 6,171,299 B1 | 1/2001 | Bonutti | |
| 6,175,758 B1 | 1/2001 | Kambin | |
| 6,187,000 B1 | 2/2001 | Davison et al. | |
| 6,338,730 B1 | 1/2002 | Bonutti et al. | |
| 6,358,266 B1 | 3/2002 | Bonutti | |
| 6,371,968 B1 | 4/2002 | Kogasaka et al. | |
| 6,432,048 B1 * | 8/2002 | Francois | 600/220 |
| 6,524,320 B2 | 2/2003 | DiPoto | |
| 6,530,880 B2 | 3/2003 | Pagliuca | |
| 6,530,926 B1 | 3/2003 | Davison | |
| 6,648,888 B1 | 11/2003 | Shluzas | |
| 6,652,553 B2 * | 11/2003 | Davison et al. | 606/190 |
| 6,800,084 B2 | 10/2004 | Davison et al. | |
| 6,811,558 B2 | 11/2004 | Davison et al. | |
| 6,821,243 B2 | 11/2004 | Pagliuca et al. | |
| 6,837,889 B2 | 1/2005 | Shluzas | |
| 6,837,891 B2 | 1/2005 | Davison et al. | |
| 7,001,397 B2 | 2/2006 | Davison et al. | |
| 7,004,947 B2 | 2/2006 | Shluzas et al. | |
| 7,033,369 B2 | 4/2006 | Davison et al. | |
| 7,056,321 B2 | 6/2006 | Pagliuca et al. | |
| 7,066,937 B2 | 6/2006 | Shluzas | |
| 7,108,705 B2 | 9/2006 | Davison et al. | |
| 7,144,393 B2 | 12/2006 | DiPoto et al. | |
| 7,223,278 B2 | 5/2007 | Davison et al. | |
| 2003/0014068 A1 | 1/2003 | Bonutti et al. | |
| 2003/0191371 A1 | 10/2003 | Smith et al. | |
| 2004/0097907 A1 | 5/2004 | DiPoto | |
| 2004/0236317 A1 | 11/2004 | Davison | |

FOREIGN PATENT DOCUMENTS

WO        0154560        8/2001

OTHER PUBLICATIONS

Endius, Atavi Atraumatic Spine Fusion System Marketing Bulletin, "How Do I Decompress Using Atavi System?", Mar. 4, 2002.

Endius, Atavi Atraumatic Spine Fusion System Marketing Bulletin, "Minimally Invasive Update on Danek," Apr. 12, 2002.

Foley et al., "Percutaneous Pedicle Screw Fixation of the Lumbar Spine," Neurosurg. Focus, 4 (10): 1-8, Apr. 2001.

Guiot et al., "A Minimally Invasive Technique for Decompression of the Lumbar Spine," 4 (27): 432-438, 2002.

Kambin, "Arthroscopic Lumbar Interbody Fusion," Spine Care White AH, 77: 1055-1056, 1995.

Kambin, "Posterolateral Percutaneous Lumbar Interbody Fusion," Arthroscopic Microdiscectomy, Minimal Intervention In Spinal Surgery, 9: 117-121, 1991.

MED presentation materials, "MicroEndoscopic Discectomy System," 33 pgs., 1997.

Medtronic SOFAMOR DANEK, "Minimal Access Spinal Technologies," Orthopedics Today, 1-20, 2002.

Medtronic SOFAMOR DANEK, "METRx Microdiscectomy Surgical Technique," as described by Donald L. Hilton Jr., M.D., F.A.C.S. and Sylvain Palmer, F.A.C.S., 19 pgs., 2001.

Medtronic SOFAMOR DANEK, "The Next Step in Minimally Invasive Discectomy Utilizing the Operating Microscope," 2 pgs., 2000.

Medtronic SOFAMOR DANEK, "An Evolution in Minimally Invasive Spine Surgery," METRx, MicroEndoscopic Discectomy, 6 pgs., 1999.

Stauber et al., "Pedicle Screw Placement with Intrasseous Endoscopy," SPINE, 1 (19): 57-61, 1994.

* cited by examiner

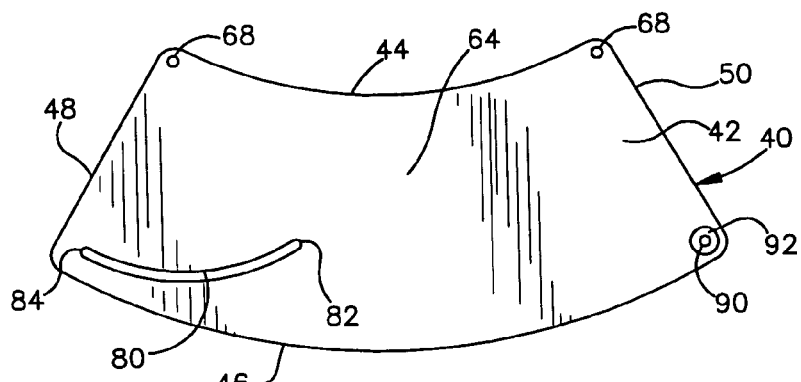
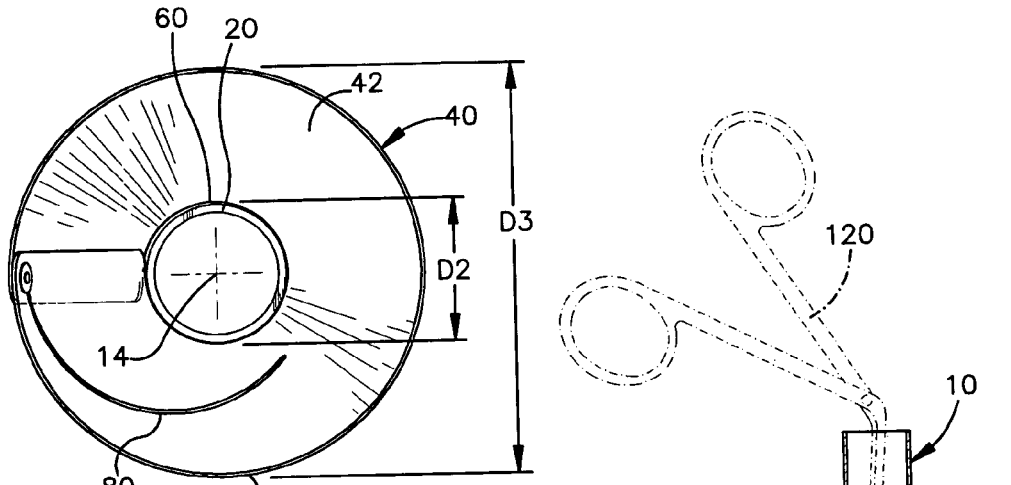
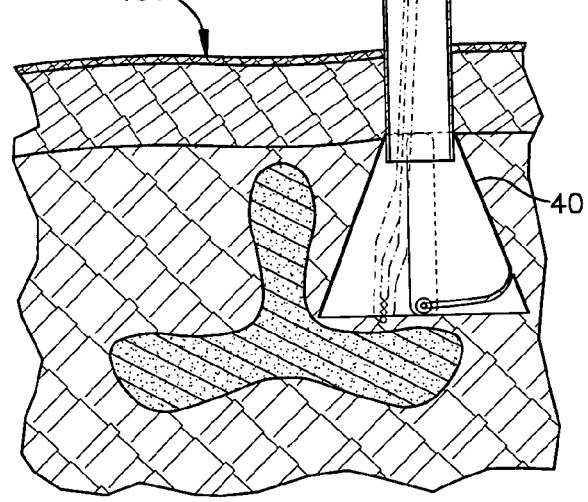

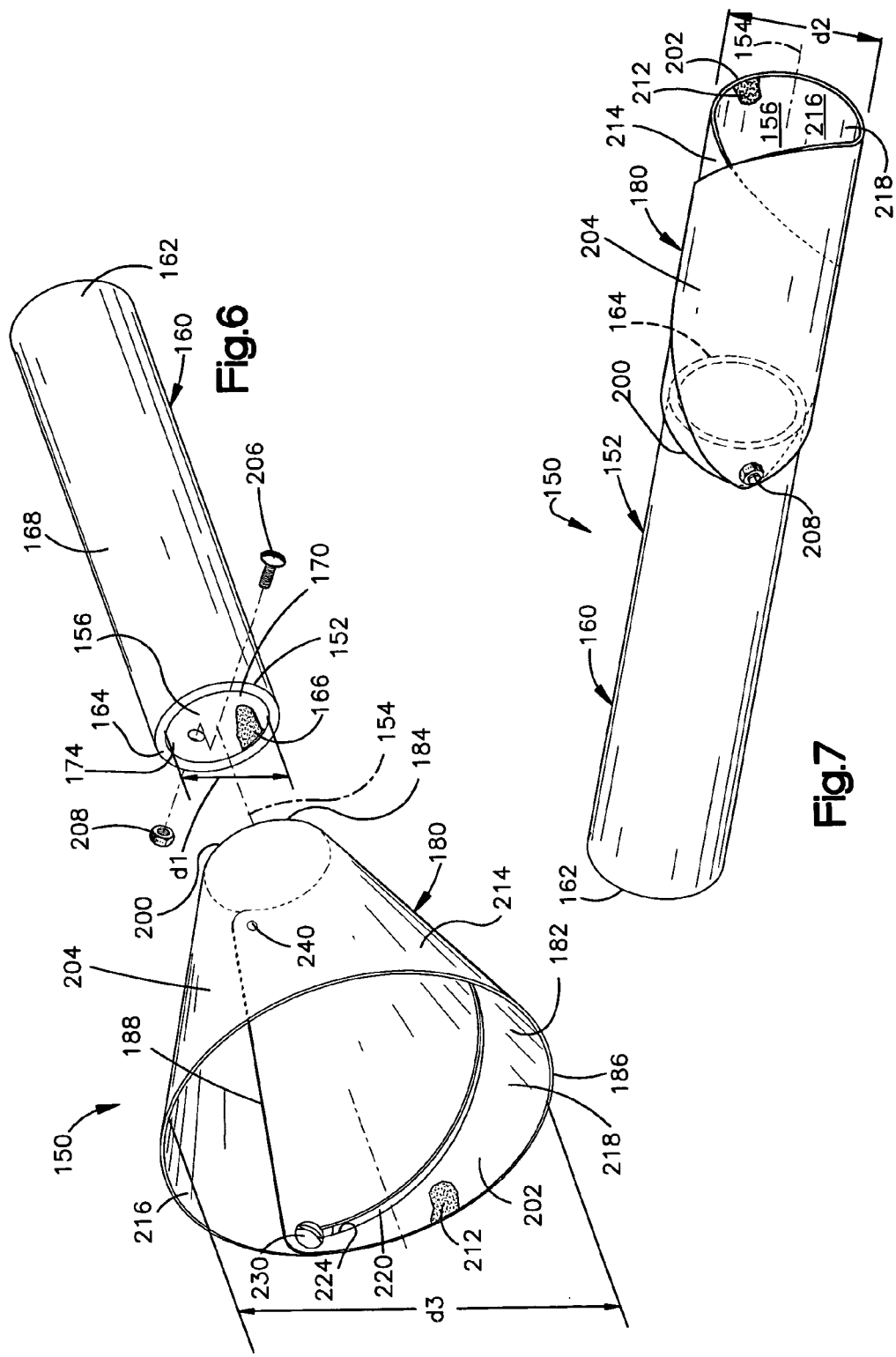

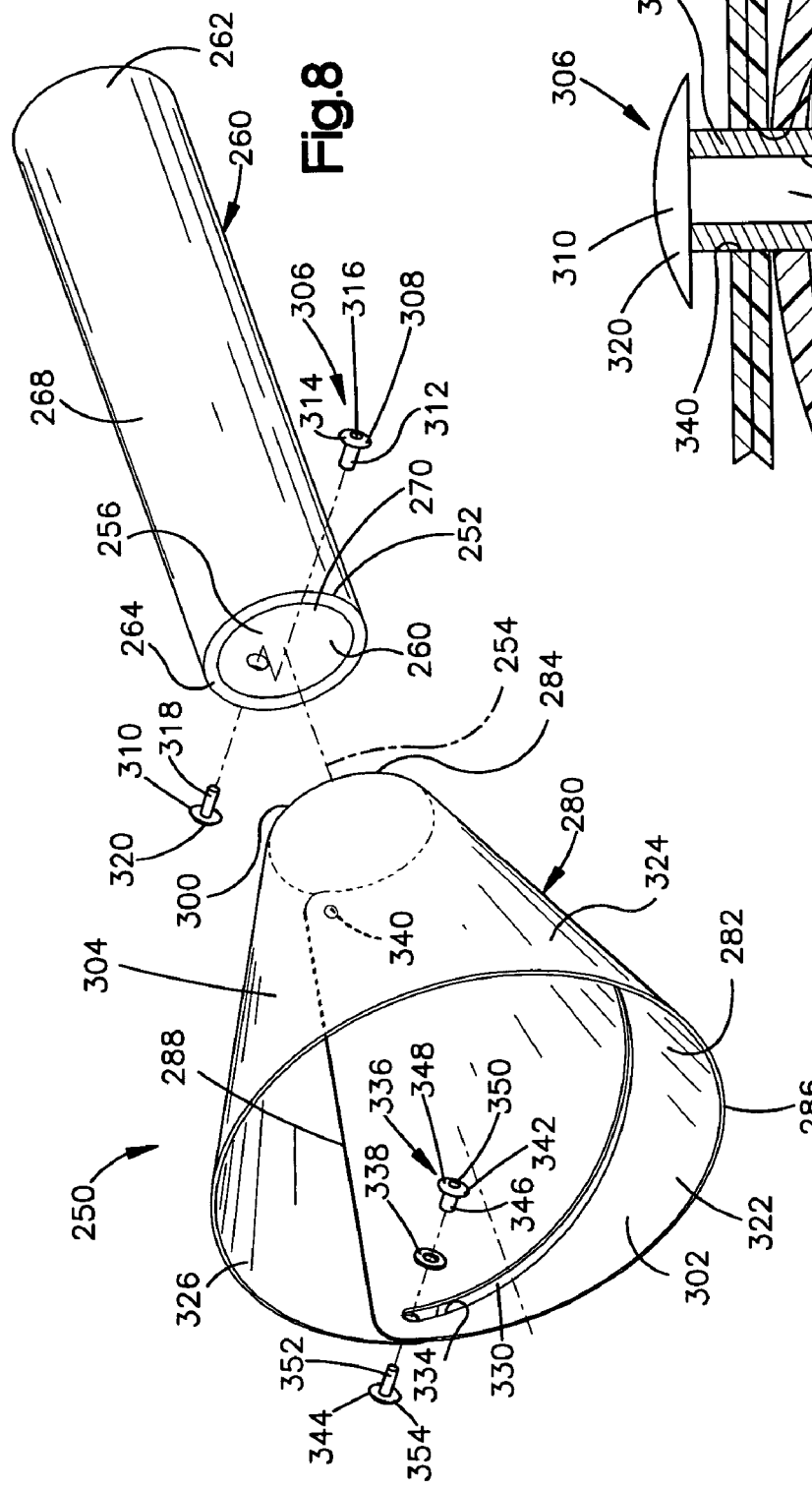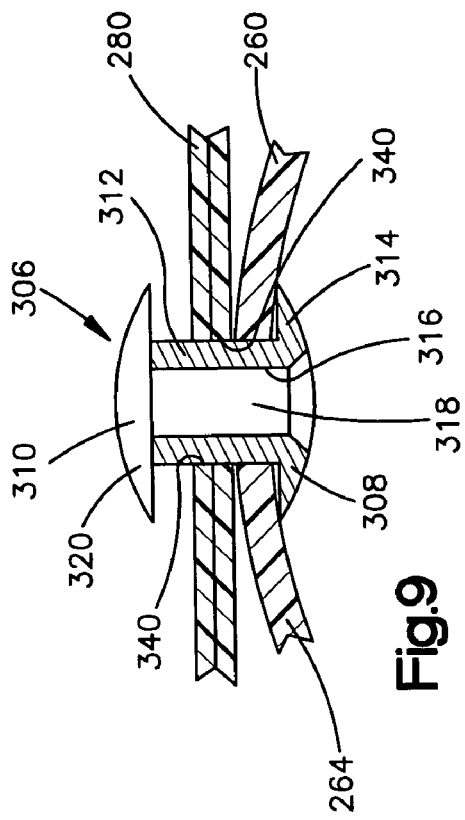

US 7,682,370 B2

SURGICAL TOOL FOR USE IN EXPANDING A CANNULA

CROSS-REFERENCE TO RELATED APPLICATION

This application is a continuation-in-part of U.S. patent application Ser. No. 09/906,463, filed on Jul. 16, 2001 now U.S. Pat. No. 6,652,553, which is a continuation-in-part of U.S. patent application Ser. No. 09/772,605, filed on Jan. 30, 2001 now U.S. Pat. No. 6,800,084 which is a continuation-in-part of U.S. patent application Ser. No. 09/137,335, filed Aug. 20, 1998, now U.S. Pat. No. 6,187,000, issued Feb. 13, 2001.

FIELD OF THE INVENTION

The present invention relates to a cannula or tubular structure for receiving surgical instruments for performing a surgical procedure on a body, and more specifically, to a surgical tool for use in expanding the tubular structure.

BACKGROUND OF THE INVENTION

Endoscopic surgical techniques allow a surgical procedure to be performed on a patient's body through a relatively small incision in the body and with a limited amount of body tissue disruption. Endoscopic surgery typically utilizes a tubular structure known as a cannula which is inserted into a small incision in the body. The cannula holds the incision open and serves as a conduit extending between the exterior of the body and the local area inside the body where the surgery is to be performed.

Due to the relatively small size of the passage into the body which is defined by the cannula, certain surgical procedures, such as posterior disectomies and procedures using steerable surgical instruments, have been difficult to perform using endoscopic techniques.

SUMMARY OF THE INVENTION

The present invention is a surgical tool for use in expanding a tubular structure. The tubular structure has an inner surface defining a passage through the tubular structure for receiving surgical instruments. The surgical tool includes a first leg having a first end engageable with the inner surface of the tubular structure. A second leg has a second end engageable with the inner surface of the tubular structure. The first and second ends are movable away from each other to apply a radially outwardly directed force to the inner surface of the tubular structure and cause expansion of the tubular structure to increase a cross-sectional area of the passage along a portion of the passage.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 3 is a schematic end view showing the cannula of FIG. 1 in the expanded condition;

FIG. 4 is a rollout view of a part of the cannula of FIG. 1;

FIG. 5 is a schematic sectional view of the cannula of FIG. 1 during a surgical procedure;

FIG. 6 is a perspective view of a part of another embodiment of a surgical cannula, the cannula being shown in an expanded condition;

FIG. 7 is a perspective view of the part of the cannula of FIG. 6, the cannula being shown in a contracted condition;

FIG. 8 is a perspective view of a part of another embodiment of a surgical cannula, the cannula being shown in an expanded condition;

FIG. 9 is a sectional view of a portion of the cannula of FIG. 8 showing a rivet connecting a first tubular portion to a second tubular portion;

DESCRIPTION OF THE INVENTION

The present invention is directed to a surgical tool for use in expanding a tubular structure or cannula for performing a surgical procedure on the body of a patient. The present invention is applicable to a variety of surgical procedures in which endoscopic surgical techniques are used.

Figure 1:
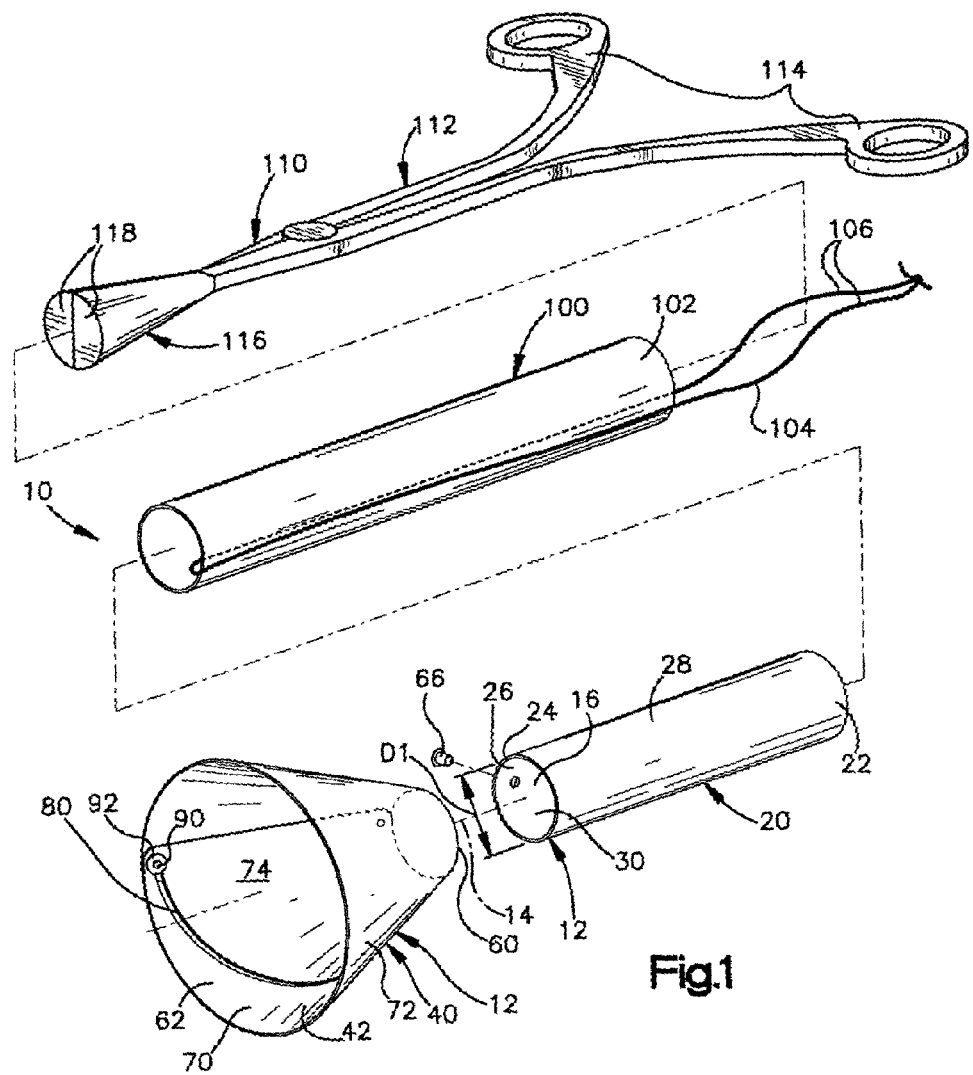
FIG. 1 is an exploded perspective view of a surgical cannula with a surgical tool constructed in accordance with a first embodiment of the present invention, the cannula being shown in an expanded condition.

FIG. 1 illustrates a cannula 10. The cannula 10 is a tubular structure 12 centered on an axis 14. The tubular structure 12 defines a passage 16 through the cannula 10. Surgical instruments are inserted into the body during endoscopic surgery through the passage 16.

The tubular structure 12 comprises a first tubular portion 20 and a second tubular portion 40 attached to the first tubular portion. The first tubular portion 20 is preferably made of a length of stainless steel tubing, but could alternatively be made of another suitable material such as a radiolucent material. The first tubular portion 20 has a proximal end 22 and a distal end 24. Parallel cylindrical inner and outer surfaces 26 and 28, respectively, extend between the ends 22, 24 of the first tubular portion 20. The inner surface 26 defines a first passage portion 30 of the passage 16 through the cannula 10. The first passage portion 30 has a diameter D1 which is preferably in the range from 10 mm to 30 mm or approximately 0.4 inches to approximately 1.2 inches.

The second tubular portion 40 of the tubular structure 12 is attached to the distal end 24 of the first tubular portion 20. The second tubular portion is preferably made from stainless steel, but could alternatively be made from another suitable material such as a radiolucent material.

As best seen in the rollout view of FIG. 4, the second tubular portion 40 comprises an arcuate segment 42 of sheet stock. The arcuate segment 42 includes first and second arcuate edges 44 and 46, respectively, and first and second planar edges 48 and 50, respectively. The first and second planar edges 48 and 50 are rolled in an overlapping manner to form the tubular configuration of the second tubular portion 40.

When the second tubular portion 40 has been rolled into its tubular configuration, the first and second arcuate edges 44 and 46 define oppositely disposed first and second ends 60 and 62 (FIGS. 1 and 2), respectively, of the second tubular portion. The first and second ends 60 and 62 are connected by a central portion 64. The first end 60 of the second tubular portion 40 is attached to the distal end 24 of the first tubular portion 20 by a single suitable fastener, such as a rivet 66. The rivet 66 extends through two aligned apertures 68 (FIG. 4) at the first end 60 of the second tubular portion 40. The first end 60 of the second tubular portion 40 is pivotable about the rivet 66.

The second tubular portion 40 includes parallel inner and outer surfaces 70 and 72 (FIGS. 1 and 2), respectively, extending between the first and second ends 60 and 62. The inner surface 70 defines a second passage portion 74 of the passage 16 through the cannula 10 which extends as a continuation of the first passage portion 30 in the first tubular portion 20.

An arcuate slot 80 is formed in the second tubular portion 40 and extends between the inner and outer surfaces 70 and 72 of the second tubular portion. The arcuate slot 80 extends along a curvilinear path in the central portion 64 of the second tubular portion 40 toward the second end 60 of the second tubular portion. The arcuate slot 80 has a first terminal end 82 located in the central portion 64 of the second tubular portion 40. A second terminal end 84 of the arcuate slot 80 is located adjacent the intersection of the second arcuate edge 46 and the first planar edge 48 of the arcuate segment 42.

A suitable guide member, such as guide pin 90, is attached to the inner surface 70 of the second tubular portion 40 adjacent the intersection of the second arcuate edge 46 and the second planar edge 50. In the tubular configuration of the second tubular portion 40, the guide pin 90 is located in the arcuate slot 80 and is movable along the curvilinear path of the arcuate slot. A washer 92 is secured to an inner end of the guide pin 90 to retain the guide pin in the arcuate slot 80.

Figure 2:
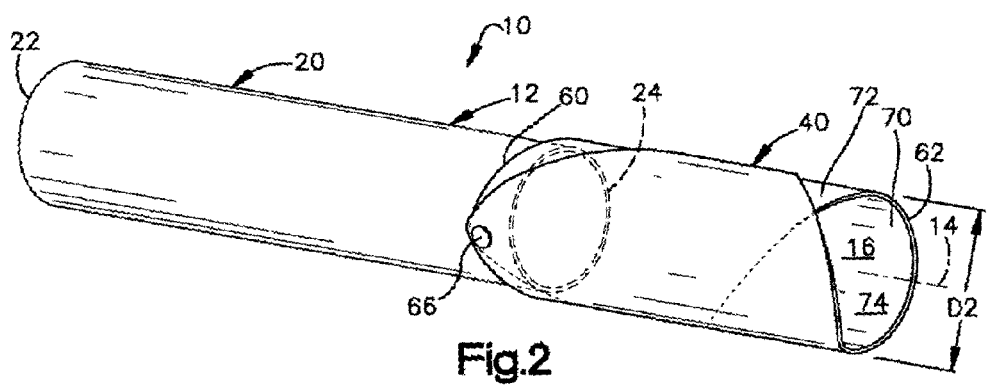
FIG. 2 is a perspective view of the cannula of FIG. 1 with parts removed for clarity, the cannula being shown in a contracted condition.

The second tubular portion 40 of the tubular structure 12 is expandable from a contracted condition shown in FIG. 2 to an expanded condition shown in FIG. 1. In the contracted condition, the guide pin 90 is located in the first terminal end 82 of the arcuate slot 80 in the second tubular portion 40 and the second passage portion 74 defined by the second tubular portion is cylindrical in shape. The second passage 74 has a generally constant diameter D2 (FIGS. 2 and 3) which is approximately equal to the diameter D1 of the first tubular portion 20. Thus, the cross-sectional area of the second passage portion 74 at the second end 62 of the second tubular portion 40, which is a function of the diameter D2, is approximately the same as the cross-sectional area at the first end 60 of the second tubular portion and is approximately the same as the cross-sectional area of the first passage portion 30 in the first tubular portion 20.

In the expanded condition, the guide pin 90 is located in the second terminal end 84 of the arcuate slot 80 in the second tubular portion 40 and the second tubular portion has a conical configuration. At the second end 62 of the second tubular portion 40, the second passage portion 74 has a diameter D3 (FIG. 3) which is larger than the diameter D2 of the second passage portion at the first end 60. Preferably, the diameter D3 of the second passage portion 74 at the second end 62 of the second tubular portion is 40% to 90% greater than the diameter D2 of the second passage portion at the first end 60. Thus, in the expanded condition, the cross-sectional area of the second passage portion 74 at the second end 62 of the second tubular portion 40, which is a function of the diameter D3, is greater than the cross-sectional area of the second passage portion at the first end 60 of the second tubular portion. Although the cross-sectional area at the second end 62 is shown as being circular in FIG. 3, it is contemplated that the cross-sectional area at the second end 62 could be any shape, such as oval shaped.

The cannula 10 includes an outer layer 100 (FIG. 1) for maintaining the second tubular portion 40 of the cannula in the contracted condition. It is contemplated that other suitable means for maintaining the second tubular portion 40 in the contracted condition could be employed. In accordance with a preferred embodiment of the present invention, the outer layer 100 comprises a section of plastic tubing 102 which is heat shrunk over both the first and second tubular portions 20 and 40 to hold the second tubular portion in the contracted condition.

In addition, a loop of polyester string 104 for tearing the heat shrink tubing 102 is wrapped around the heat shrink tubing so that it extends both underneath and on top of the tubing. An outer end 106 of the string 104 extends beyond the tubing 102.

The cannula 10 further includes an actuatable device 110 for expanding the second tubular portion 40 from the contracted condition to the expanded condition. In accordance with a first embodiment of the present invention, the actuatable device 110 comprises a manually operated expansion tool 112. The expansion tool 112 resembles a common pair of scissors and has a pair of legs 114 pivotally connected to one another. The expansion tool 112 includes a frustoconical end section 116 formed by a pair of frustoconical halves 118. Each of the frustoconical halves 118 extends from a respective one of the legs 114 of the expansion tool 112. It is contemplated that other suitable means for expanding the second tubular portion 40 toward the expanded condition could be employed, such as an inflatable balloon (not shown).

During an endoscopic surgical procedure, the cannula 10 is inserted through an incision into the body of a patient in the contracted condition. The cannula 10 is inserted through the incision using step dilation. The second tubular portion 40 is inserted inside the body. The first tubular portion 20 is inserted into the incision so that the first tubular portion extends from an exterior of the body to inside the body.

The outer end 106 of the string 104 is then manually pulled on by the surgeon. Pulling on the string 104 tears the heat shrink tubing 102. With the heat shrink tubing 102 torn, the second tubular portion 40 of the cannula 10 is thereby released for expansion toward the expanded condition.

Next, the expansion tool 112 is inserted into the passage 16 in the cannula 10 until the frustoconical end section 114 is located at the second end 62 of the second tubular portion 40. The legs 114 of the expansion tool 112 are manually separated, causing the frustoconical halves 118 to separate also. As the halves 118 separate, a radially outwardly directed force is exerted on the inner surface 70 of the second tubular portion 40 by the halves 118, causing the second tubular portion to expand toward the expanded condition.

Under the force of the expanding expansion tool 112, the guide pin 90 slides from the first terminal end 82 of the arcuate slot 80 to the second terminal end 84 of the arcuate slot to permit the expansion of the second tubular portion 40. The expansion tool 112 can be rotated about the axis 14 to ensure that the second tubular portion 40 of the cannula 10 is completely expanded to the expanded condition. The expansion tool 112 is then collapsed and removed so that one or more surgical instruments (indicated schematically at 120 in FIG. 5) can be received through the cannula 10 and inserted into a patient's body 130.

The expandable second tubular portion 40 of the cannula 10 provides a significantly larger working area for the surgeon inside the body 130 within the confines of the cannula. As a result, the simultaneous use of a number of endoscopic surgical instruments, including but not limited to steerable instruments, shavers, dissectors, scissors, forceps, retractors, dilators, and endoscopes, is made possible by the expandable cannula 10.

Figure 10:
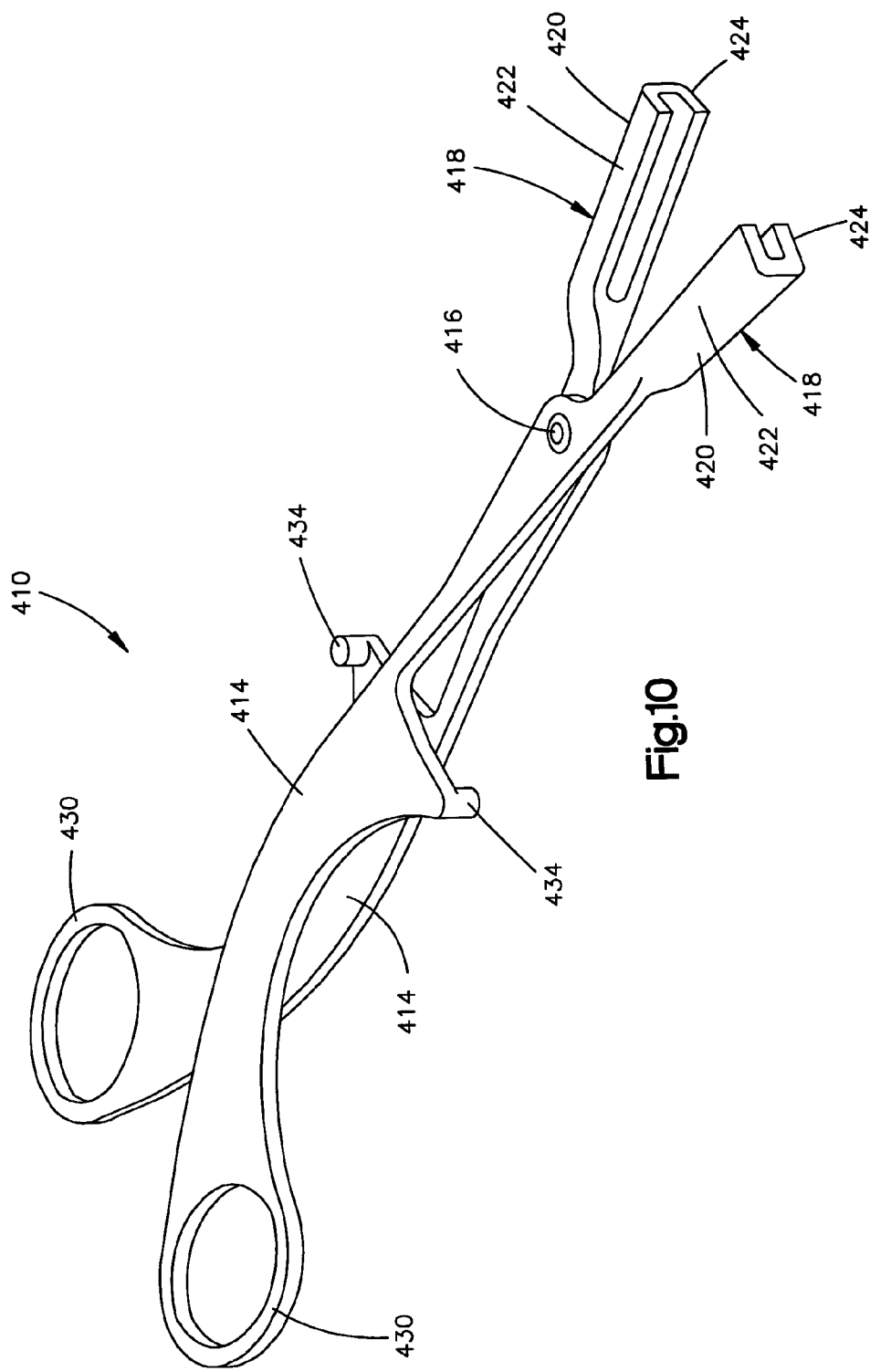
FIG. 10 is a perspective view of a surgical tool constructed in accordance with a second embodiment of the present invention.

A surgical tool 410 constructed according to a second embodiment of the present invention is illustrated in FIG. 10. The surgical tool 410 resembles a common pair of scissors and has a pair of legs 414 pivotally connected to each other by a pivot connection 416. Each of the legs 414 has an end 418 with a tapered outer surface 420. Each of the ends 418 has a generally U-shaped cross-section with outer surfaces 422 and 424. The surfaces 422 and 424 extend generally parallel to each other and transverse to the tapered surface 420.

The legs 414 have handles 430 opposite the ends 418. The handles 430 may be grasped by a surgeon to move the ends 418 away from each other. The handles 430 are moved toward each other to move the ends 418 away from each other. Each of the legs 414 has a stop 434 that engages the other leg to limit the movement of the ends 418 away from each other.

The expansion tool 410 is inserted into the passage 16 in the cannula 10 until the ends 418 are located at the second end 62 of the second tubular portion 40. The legs 418 of the expansion tool 410 are manually separated by moving the handles 430 toward each other. As the handles 430 are moved toward each other, the ends 418 separate. As the ends 418 separate, a radially outwardly directed force is exerted on the inner surface 70 of the second tubular portion 40 by the ends 418, causing the second tubular portion to expand toward the expanded condition. Under the force of the expanding expansion tool 410, the guide pin 90 slides from the first terminal end 82 of the arcuate slot 80 toward the second terminal end 84 of the arcuate slot to permit the expansion of the second tubular portion 40. The expansion tool 410 can be rotated about the axis 14 to ensure that the second tubular portion 40 of the cannula 10 is completely expanded to the expanded condition. The expansion tool 410 is then collapsed and removed so that one or more surgical instruments can be received through the cannula 10 and inserted into a patient's body.

A surgical tool 510 constructed according to a third embodiment of the present invention is illustrated in FIGS. 11-16. The surgical tool 510 (FIGS. 11-12) includes a tubular housing 512. The housing 512 has a tubular first or distal member 514 and a tubular second or proximal member 516. A tubular intermediate member 518 interconnects the proximal and distal members 514 and 516. The distal and proximal members 514 and 516 are welded to the intermediate member 518. It is contemplated that the proximal and distal members 514 and 516 may be connected to the intermediate member 518 in any suitable manner.

The intermediate member 518 includes a first or distal end portion 522 connected to the distal member 514. The intermediate member 518 has a second or proximal end portion 524 connected to the proximal member 516. The intermediate portion 518 (FIGS. 14-15) is tubular and defines a passage 526 extending through the intermediate member. The passage 526 has a first portion 528 with a first diameter and a second portion 529 in the second end portion 524 with a second diameter larger than the first diameter.

The intermediate member 518 includes a plurality of annular grooves 530 (FIGS. 11-12) in the outer surface that define a plurality of positions for connecting a depth limiter 532 to the intermediate member 518. Although the intermediate member 518 is shown with seven annular grooves 530, it is contemplated that the intermediate member may have any member of annular grooves. The depth limiter 532 engages a proximal end of the tubular structure 12 to limit the depth that the surgical tool 510 extends into the tubular structure 12. Accordingly, the depth limiter 532 is placed in a desired position on the intermediate member 518 depending on the length of the tubular structure 12.

The distal member 514 (FIG. 14) includes a first end portion 538 that extends into the passage 526 in the intermediate member 518 to connect the distal member with the intermediate member. The first end portion 538 of the distal member 514 is tubular and has an outer diameter substantially equal to the diameter of the first portion 528 of the passage 526. The first end portion 538 defines a passage 540 which is a continuation of the passage 526.

The distal member 514 (FIGS. 11-12) includes a second end portion 542 having an outer diameter equal to the outer diameter of the intermediate member 518. The second end portion 542 includes a pair of axially extending projections 544. The projections 544 extend generally parallel to each other and define a channel 546 between them. The channel 546 is a continuation of the passage 540 in the first end portion 538. Each of the projections 544 (FIG. 12) has a through-hole 550 that intersects the channel 546.

The proximal member 516 (FIG. 15) includes a first end portion 548 that extends into the second portion 529 of the passage 526 in the second end portion 524 of the intermediate member 518. The first end portion 548 is tubular and has an outer diameter substantially equal to the diameter of the second portion 529 of the passage 526. The first end portion 548 defines a passage 549 which is a continuation of the passage 526.

Figure 13:
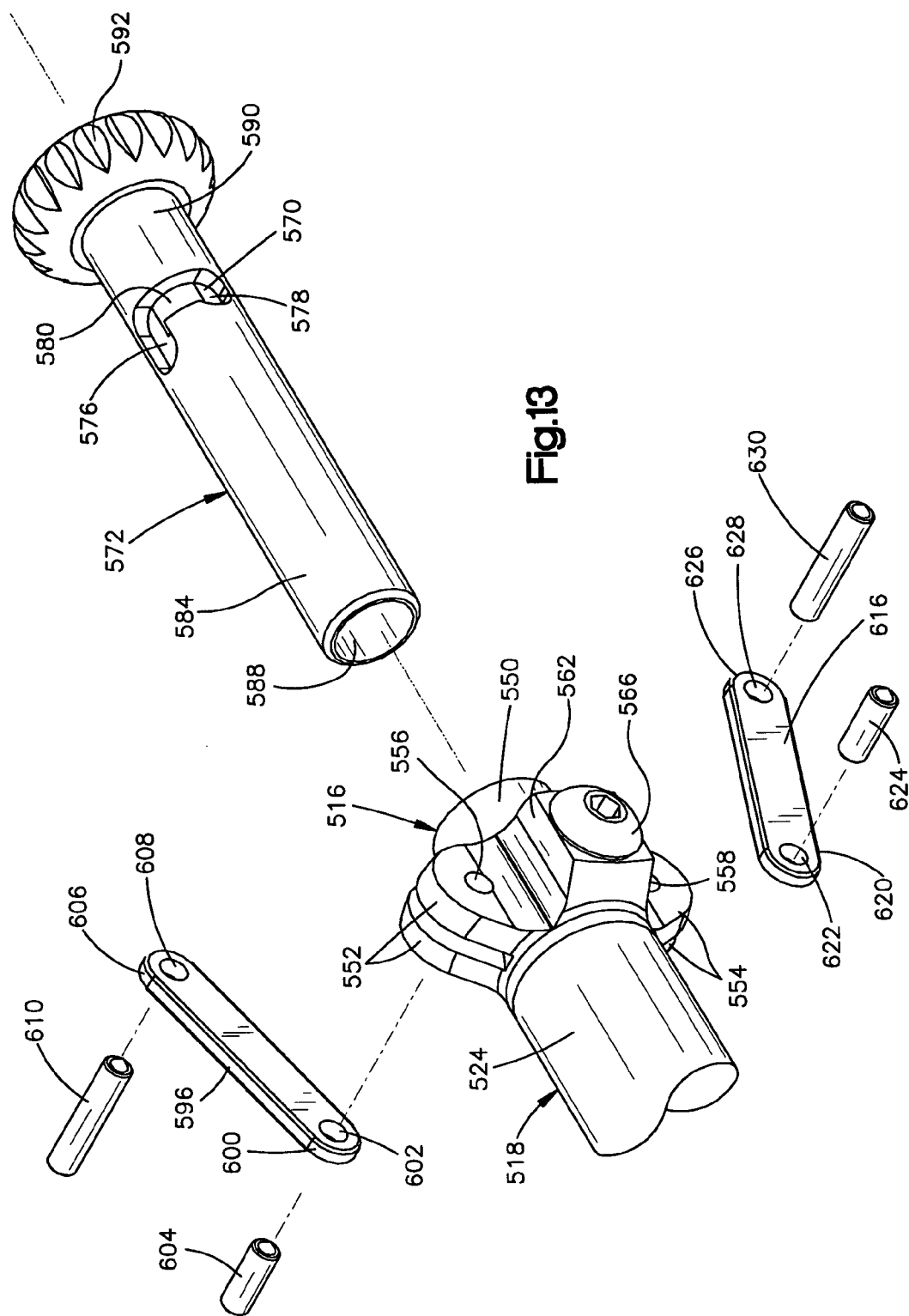
FIG. 13 is an enlarged exploded view of a portion of the surgical tool of FIG. 11.
Figure 14:
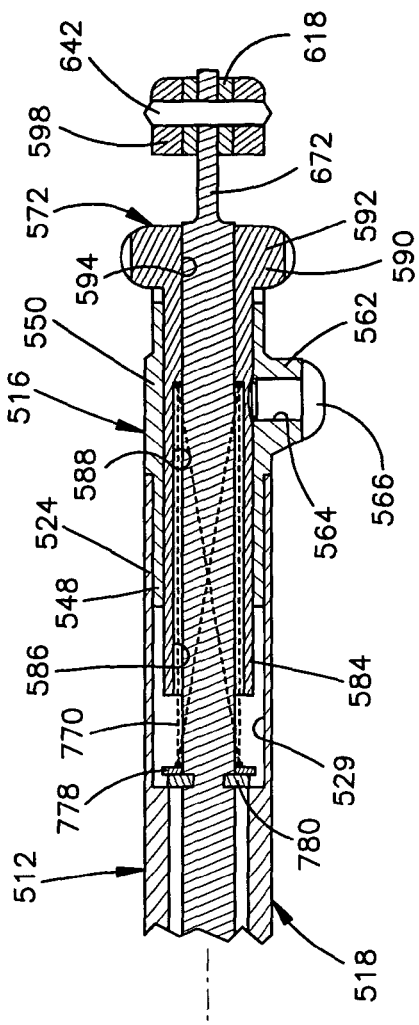
FIG. 14 is a cross-sectional view of the surgical tool of FIG. 11.
Figure 15:
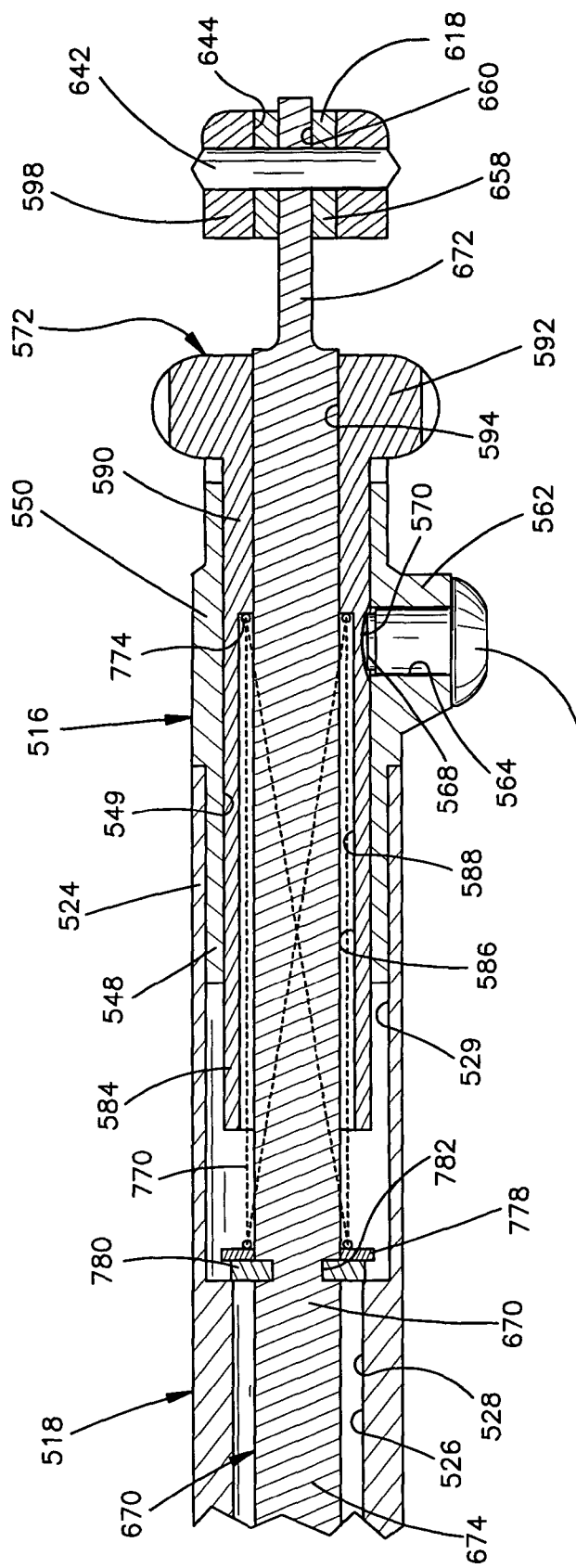
FIG. 15 is an enlarged cross-sectional view of a portion of the surgical tool of FIG. 11.

The proximal member 516 (FIGS. 11-13) includes a second end portion 550 that extends from the first end portion 548. The second end portion 550 includes a pair of radially extending flanges 552. A pair of radially extending flanges 554 extend from the second end portion 550 opposite the flanges 552. Each of the flanges 552 has a through-hole 556, one of which is shown in FIG. 13. Each of the flanges 554 has a through-hole 558, one of which is shown in FIG. 13.

A radially extending projection 562 extends generally perpendicular to the flanges 552 and 554. The radially extending projection 562 (FIG. 15) has a radially extending threaded opening 564. The opening 564 intersects the passage 549 in the proximal member 516.

A positioning screw 566 threadably engages the opening 564. The screw 566 has an end portion 568 that extends into a recess 570 in a sleeve 572. The positioning screw 566 holds the sleeve 572 in any one of a plurality of positions relative to the housing 512.

The recess 570 (FIG. 13) in the sleeve 572 has first and second axially extending portions 576 and 578. A radially extending connecting portion 580 extends between proximal ends of the portions 576 and 578. The first axially extending portion 576 extends axially from the connecting portion 580 a distance which is larger than the distance that the second axially extending portion 578 extends from the connecting portion 580. The end portion 568 of the screw 566 may be positioned in either one of the axially extending portions 576 and 578 of the recess 570. Although the recess 570 is shown with two axially extending portions 576 and 578, it is contemplated that the recess may have any number of axially extending portions.

A first tubular end portion 584 (FIG. 15) of the sleeve 572 extends into the passage 549 of proximal member 516. The end portion 584 has an outer diameter that is smaller than the diameter of the passage 549 in the proximal member 516 to permit movement of the sleeve 572 relative to the housing 512. The end portion 584 defines a larger diameter portion 586 of a passage 588 through the sleeve 572.

A second end portion 590 (FIGS. 13-15) of the sleeve 572 includes a radially extending knurled portion 592. The knurled portion 592 may be manually grasped to move the sleeve 572 relative to the proximal member 516. The second end portion 590 (FIG. 15) defines a smaller diameter portion 594 of the passage 588.

A first link 596 (FIGS. 12-13) is pivotally connected to the flanges 552 on the proximal member 516 and to a first handle 598. The link 596 has a first end 600 with a through-hole 602. The first end 600 of the link 596 extends between the flanges 552. A pivot pin 604 extends through the through-hole 602 and the through-holes 556 in the flanges 552 to pivotally connect the link 596 to the flanges 552. A second end 606 of the link 596 has a through-hole 608. A pivot pin 610 extends through through-holes 612 in the handle 598 and the through-hole 608 to pivotally connect the link 596 to the handle 598.

A second link 616 is pivotally connected to the flanges 554 on the proximal member 516 and to a second handle 618. The link 616 has a first end 620 with a through-hole 622. The first end 620 of the link 616 extends between the flanges 554. A pivot pin 624 extends through the through-holes 558 in the flanges 554 and the through-hole 622 to pivotally connect the link 616 to the flanges 554. A second end 626 of the link 616 has a through-hole 628. A pivot pin 630 extends through through-holes 632 in the handle 618 and the through-hole 628 to pivotally connect the link 616 to the handle 618.

The first handle 598 (FIGS. 11-12) has a first end portion 640 pivotally connected to the second handle 618 by a pivot pin 642. The first end portion 640 of the handle 598 has a channel 644 (FIG. 15) into which the second handle 618 extends. The pivot pin 642 extends through through-holes in the first end portion 640 that intersect the channel 644 and a through-hole in the second handle 618 to pivotally connect the first and second handles 598 and 618. The second end portion 606 (FIG. 12) of the link 596 is also received in the channel 644. The through-holes 612 in the handle 598 intersect the channel 644 and receive the pivot pin 610 to pivotally connect the link 596 to the handle 598.

The handle 598 (FIGS. 11-12) includes a second end portion 648 extending axially from the first end portion 640. The second end portion 648 extends in a distal direction from the first end portion 640. The second end portion 648 of the handle 598 has gripping features located on an upper surface 650.

The second handle 618 (FIG. 12) has a first end portion 656 pivotally connected to the first end portion 640 of the first handle 598. The first end portion 656 has a portion 658 with a width less than the width of the channel 644 that extends into the channel 644 in the first handle 598. The pivot pin 642 extends through through-holes in the first handle 518 and a through-hole in the portion 658 of the second handle 618 to pivotally connect the handles to each other.

The first end portion 656 (FIG. 12) of the second handle 618 also includes a channel 660. The second end portion 626 of the link 616 extends into the channel 660. The through-holes 632 in the second handle 618 intersect the channel 660 and receive the pivot pin 630 to pivotally connect the link 616 to the second handle 618.

The second handle 618 (FIGS. 11-12) includes a second end portion 662 extending axially from the first end portion 656. The second end portion 662 extends in a distal direction from the first end portion 656. The second end portion 662 of the handle 618 has gripping features located on a lower surface 664.

The first end portions 640 and 656 (FIGS. 12 and 15) of the handles 598 and 618 are also pivotally connected to an actuator 670 by the pivot pin 642. The actuator 670 has a first flattened end portion 672 with a through-hole 674. The first end portion 672 of the actuator 670 extends into the channel 660 in the handle 618. The pivot pin 642 extends through the through-hole 674 in the actuator 670 and the through-holes in the handles 598 and 618 to pivotally connect the actuator to the handles.

The actuator 670 (FIGS. 14-15) extends axially through the passage 588 in the sleeve 572, the proximal member 516, and the passage 526 in the intermediate member 518 into the channel 546 in the distal member 514. The actuator 670 has a cylindrical central portion 674 extending between the first flattened end portion 672 and a second flattened end portion 678 that extends into the channel 546. The central portion 674 has a diameter smaller than the smaller diameter portion 594 of the passage 588 in the sleeve 572 and smaller than the diameter of the passage 540 in the distal member 514 to permit axial movement of the actuator 670.

The second end portion 678 (FIG. 12) of the actuator 670 has a through-hole 680 for pivotally connecting the second end portion 678 with linking members 686 and 688. The second end portion 678 extends between the linking members 686 and 688. The first linking member 686 has a first end portion 690 with a through-hole 692. The second linking member 688 has a first end portion 694 with a through-hole 696. A pivot pin 698 extends through the through-holes 692 and 696 in the linking members 686 and 688 and through the through hole 680 in the actuator 670 to pivotally connect the linking members to the actuator.

The linking member 686 has a second end portion 702 with a cylindrical portion 704 extending toward the linking member 688. The second linking member 688 has a second end portion 706 with a cylindrical portion 708 extending toward the first linking member 686. The cylindrical portion 704 on the first linking member 686 extends into a through-hole 720 in a first leg or jaw 722 to pivotally connect the leg to the first linking member 686. The cylindrical portion 708 on the second linking member 688 extends into a through-hole 724 in a second leg or jaw 726 to pivotally connect the second leg 726 to the linking member 688.

The jaw 722 has a first end 730 through which the through-hole 720 extends. A second through-hole 732 extends through the first end 730 of the jaw 722. A second end 734 of the leg or jaw 722 extends from the first end 730. The second end 734 has a radial width greater than the width of the first end 730.

The second leg or jaw 726 has a first end 746 through which the through-hole 724 extends. The first end 746 also includes a through-hole 748. A second end 752 of the leg 726 extends from the first end 746. The second end 752 has a radial width which is greater than the radial width of the first end 746.

The first ends 730 and 746 of the legs or jaws 722 and 726 extend into the channel 546 between the projections 544. A pivot pin 760 extends through the through-holes 748 and 732 in the first and second legs 722 and 726. The pivot pin 760 also extends into the through-holes 550 in the distal member 514 to pivotally connect the legs 722 and 726 to each other and the distal member 514. Accordingly, axial movement of the actuator 670 relative to the housing 512 causes pivotal movement of the legs 722 and 726 relative to the distal member 514.

The actuator 670 (FIGS. 12 and 14-15) extends through a spring 770 located in the portion 586 of the passage 588 in the sleeve 572. The spring 770 extends from a shoulder 774 on the sleeve 572 to a washer 778 on the actuator 670. A C-shaped snap ring 780 extends into an annular groove 782 on the actuator 670 to hold the washer 778 in an axial position on the actuator. The spring 770 engages the washer 778 and urges the snap ring 780 into engagement with a shoulder 782 on the intermediate member 518. The spring 770 biases the actuator 670 in a distal direction. Accordingly, the spring 770 biases the handles 598 and 618 to pivot away from each other and the legs 722 and 726 to pivot toward each other.

Upon pivotal movement of the handles 598 and 618 toward each other, the actuator 670 moves in a proximal direction to compress the spring 770. The proximal movement of the actuator 670 causes the first ends 690 and 694 of the link members 686 and 688 to move in a proximal direction. Movement of the link members 686 and 688 in a proximal direction causes the legs 722 and 726 to pivot relative to the distal member 514 away from each other. When the handles 598 and 618 are released, the spring 770 moves the actuator 670 in a distal direction to pivot the legs 722 and 726 toward each other and the handles 598 and 618 away from each other.

The distance that the legs 722 and 726 move away from each other is controlled by the distance that the actuator 670 moves in the proximal direction. The distance that the actuator 670 moves in the proximal direction is defined as distance between the washer 778 on the actuator and the first end portion 584 of the sleeve 572. The sleeve 572 has a plurality of axial positions relative to the housing 512 and the actuator 670. When the screw 566 is located in the axially extending portion 578 of the recess 570 in the sleeve, the first end portion 584 of the sleeve 572 is located closer to the washer 778 than when the screw extends into the axially extending portion 576 of the recess 570. When the screw 566 is located in the axially extending portion 578, the legs 722 and 726 move away from each other a first distance. When the screw 566 is located in the axially extending portion 576, the legs 722 and 726 move away from each other a second distance larger than the first distance.

The axial position of the sleeve 572 is adjusted by moving the sleeve axially in a distal direction relative to the housing 512 to compress the spring 770. The sleeve 572 is moved in the distal direction until the screw 566 is aligned with the radially extending portion 580 of the recess 570. The sleeve 572 is then rotated relative to the housing 512 and actuator 670 to position the screw 566 in the desired axially extending portion 576 or 578 of the recess 570. When the screw 566 is positioned in the desired axially extending portion 576 or 578, the sleeve is released and the spring 770 moves the sleeve in a proximal direction. The screw 566 holds the sleeve 572 in the desired position relative to the housing 512 and the actuator 670.

The depth limiter 532 (FIGS. 11-12 and 16) is positioned along the housing 512 to limit the depth that the surgical tool 510 may be inserted into the cannula or tubular structure 12. The depth limiter includes first and second housing portions 800 and 802. The housing member 800 (FIG. 16) has four through-holes 804 through which screws 806 extend. The screws 806 threadably engage openings 808 in the second housing member 802 to connect the housing members 800 and 802 to each other.

The housing member 800 has a circular opening 812 through which the housing 512 extends. The housing member 802 has a circular opening 814 through which the housing 512 extends. The openings 812 and 814 have a diameter larger than the diameter of the housing 512.

A locking member 818 is slidably disposed within the housing members 800 and 802. The locking member 818 has an opening 820 which is aligned with the openings 812 and 814 in the housing members 800 and 802. The opening 820 has a first end 822 with a width greater than the diameter of the housing 512. Accordingly, when the end portion 822 of the opening 820 is aligned with the openings 812 and 814, the depth limiter 532 can move relative to the housing 512.

The opening 820 in the locking member 818 has a second end 824 with a width smaller than the diameter of the housing 512. The locking member 818 has side portions 826 that extend into the opening 820 to define the second end 824. The side portions 826 of the locking member 818 extend into the grooves 530 and the housing 512 to prevent movement of the depth limiter 532 relative to the housing 512.

Figure 16:
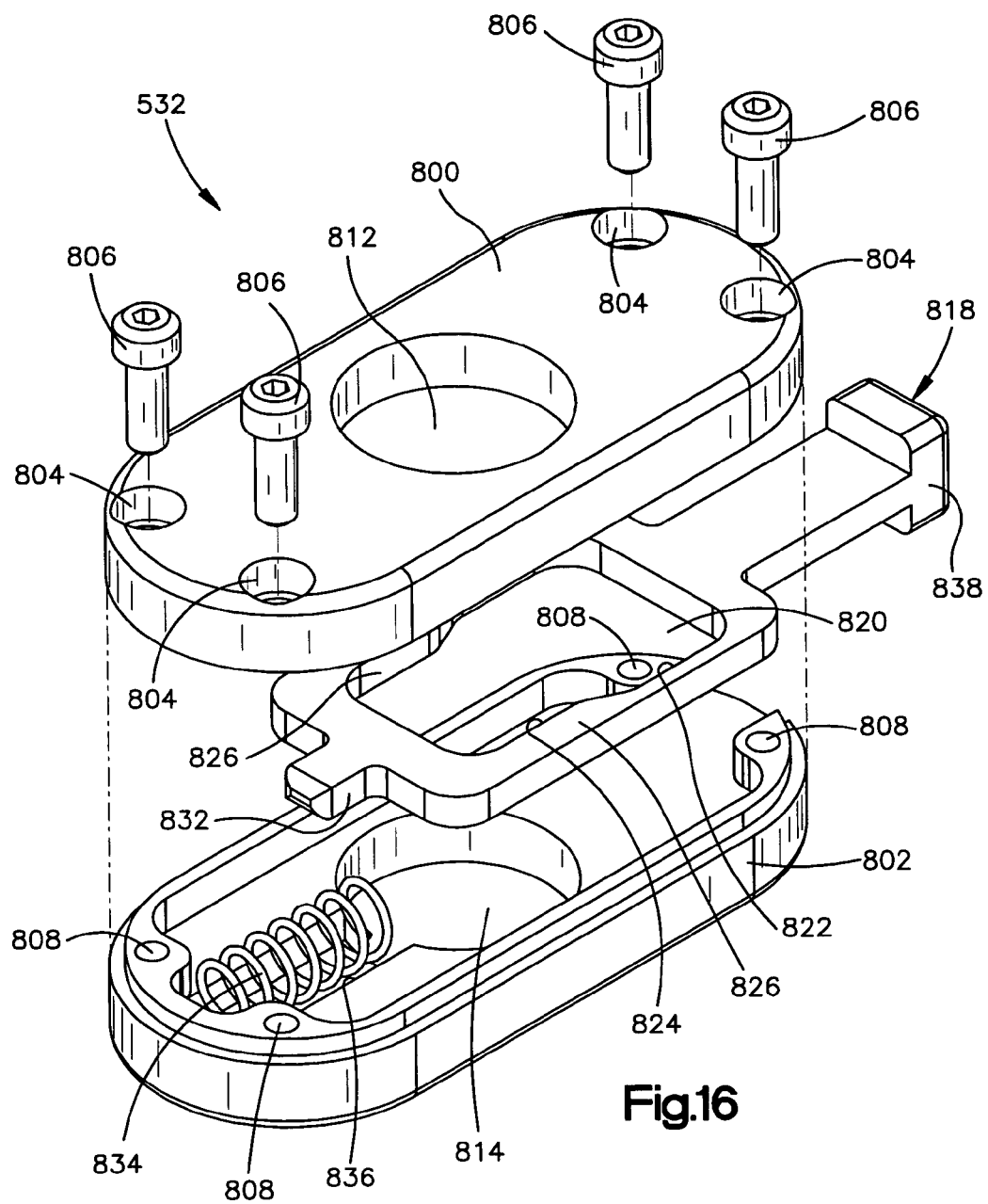
FIG. 16 is an exploded view of a depth limiter of the surgical tool of FIG. 11.

The locking member 818 has a nose 832 that extends into a coil spring 834. The spring 834 biases the locking member 818 to align the second end 824 of the opening 820 with the openings 812 and 814 in the housing members 800 and 802. The spring 834 is located in recesses 836, one of which is shown in FIG. 16, in the housing members 800 and 802.

A button portion 838 of the locking member 818 extends out of the housing members 800 and 802. The button portion 838 may be depressed to move the locking member 818 so that the first end 822 of the opening 820 is aligned with the openings 812 and 814 to allow positioning of the depth limiter relative to the housing 512. Upon release of the button portion 838, the spring 834 moves the second end 824 of the opening 820 into alignment with the openings 812 and 814.

When the expansion tool 510 is to be inserted into the cannula 10 the depth limiter 532 is moved to a desired position along the housing 512 in accordance with the length of the cannula. The depth limiter 532 is positioned along the housing 512 so that the ends 734 and 752 of the legs 722 and 726 are located at the second end 62 of the second tubular portion 40 when the surgical tool 510 is inserted into the tubular structure. The sleeve 572 is moved to a desired axial position in accordance with a desired amount of expansion of the second tubular portion 40.

The expansion tool 510 is inserted into the passage 16 in the cannula 10 until the depth limiter 532 engages the tubular structure 12 and the ends 734 and 752 of the legs 722 and 726 are located at the second end 62 of the second tubular portion 40. The legs 722 and 726 of the tool 510 are separated by moving the handles 598 and 618 toward each other. As the handles 598 and 618 are moved toward each other, the ends 734 and 752 separate. The ends 734 and 752 move away from each other until the washer 778 engages the sleeve 572. The maximum distance that the ends 734 and 752 move away from each other is determined by the position of the sleeve 572.

As the ends 734 and 752 separate, a radially outwardly directed force is exerted on the inner surface 70 of the second tubular portion 40 by the ends 734 and 752, causing the second tubular portion to expand toward the expanded condition. Under the force of the expanding tool 510, the guide pin 90 slides from the first terminal end 82 of the arcuate slot 80 toward the second terminal end 84 of the arcuate slot to permit the expansion of the second tubular portion 40. The tool 510 can be rotated about the axis 14 to ensure that the second tubular portion 40 of the cannula 10 is completely expanded to the expanded condition. The expansion tool 510 is then collapsed and removed so that one or more surgical instruments can be received through the cannula 10 and inserted into a patient's body.

A cannula 150 constructed according to another embodiment is illustrated in FIGS. 6-7. The cannula 150 includes a tubular structure 152 centered on an axis 154. The tubular structure 152 defines a passage 156 through the cannula 150. Surgical instruments are inserted into the body during endoscopic surgery through the passage 156.

The tubular structure 152 (FIG. 6) comprises a first tubular portion 160 and a second tubular portion 180 attached to the first tubular portion. The first tubular portion 160 is preferably made of a length of stainless steel tubing, but could alternatively be made of another suitable material, such as a radiolucent material. The first tubular portion 160 has a proximal end 162 and a distal end 164. Parallel cylindrical inner and outer surfaces 166 and 168 extend between the ends 162, 164 of the first tubular portion 160. The first tubular portion 160 has a thickness measured perpendicular to the surfaces 166 and 168 in the range of 0.02 inches to 0.04 inches or approximately 0.5 mm to approximately 1.0 mm.

The inner surface 166 defines a first passage portion 170 of the passage 156 through the cannula 150. The first passage portion 170 has a diameter d1 which is preferably in the range from 10 mm to 30 mm or approximately 0.4 inches to approximately 1.2 inches. The inner surface 166 has a non-reflective coating 174. The non-reflective coating 174 reduces glare on any video image produced by an endoscope inserted through the passage 156. It is contemplated that the inner surface 166 may not have the coating 174.

The second tubular portion 180 (FIG. 6) of the tubular structure 152 is attached to the distal end 164 of the first tubular portion 160. The second tubular portion 180 is preferably made from stainless steel, but could alternatively be made from another suitable material, such as a radiolucent material.

The second tubular portion 180 includes an arcuate segment 182 of sheet stock. The arcuate segment 182 includes first and second arcuate edges 184 and 186. The arcuate segment 182 also includes a first planar edge 188 and a second planar edge extending between the arcuate edges 184 and 186, which is not shown in FIG. 6. The first and second planar edges are rolled in an overlapping manner to form the tubular configuration of the second tubular portion 180.

When the second tubular portion 180 has been rolled into its tubular configuration, the first and second arcuate edges 184 and 186 define oppositely disposed first and second ends 200 and 202 of the second tubular portion. The first and second ends 200 and 202 are connected by a central portion 204. The first end 200 of the second tubular portion 180 is attached to the distal end 164 of the first tubular portion 160 by a suitable fastener, such as a screw 206 and nut 208 threaded on the screw. It is contemplated that the second tubular portion 180 could be connected to the first tubular portion 160 by a rivet. The screw 206 extends through two aligned apertures 240 at the first end 200 of the second tubular portion 180. The first end 200 of the second tubular portion 180 is pivotable about the screw 206.

The second tubular portion 180 includes parallel inner and outer surfaces 212 and 214 extending between the first and second ends 200 and 202. The inner surface 212 defines a second passage portion 216 of the passage 156 through the cannula 150 which extends as a continuation of the first passage portion 170 in the first tubular portion 160. The second tubular portion 180 has a thickness measured perpendicular to the surfaces 212 and 214 in the range of 0.003 inches to 0.007 inches or approximately 0.075 mm to approximately 0.18 mm. The inner surface 212 has a non-reflective coating 218. The non-reflective coating 218 reduces glare on any video image produced by an endoscope inserted through the passage 156. It is contemplated that the inner surface 212 may not have the coating 218.

An arcuate slot 220 (FIG. 6) is formed in the second tubular portion 180 and extends between the inner and outer surfaces 212 and 214 of the second tubular portion. The arcuate slot 220 extends along a curvilinear path in the central portion 204 of the second tubular portion 180 toward the end 184 of the second tubular portion. The arcuate slot 220 has a first terminal end (not shown) located in the central portion 204 of the second tubular portion 180. A second terminal end 224 of the arcuate slot 220 is located adjacent the intersection of the second arcuate edge 186 and the planar edge 188 of the arcuate segment 182.

A guide member or screw 230 is attached to the inner surface 212 of the second tubular portion 180 adjacent the intersection of the second arcuate edge 186 and the planar edge (not shown). It is contemplated that a guide pin could be used instead of the screw 230. In the tubular configuration of the second tubular portion 180, the guide member 230 is located in the arcuate slot 220 and is movable along the curvilinear path of the arcuate slot.

The second tubular portion 180 of the tubular structure 152 is expandable from a contracted condition, shown in FIG. 7, to an expanded condition, shown in FIG. 6. In the contracted condition (FIG. 7), the guide member 230 is located in the first terminal end (not shown) of the arcuate slot 220 in the second tubular portion 180 and the second passage portion 216 defined by the second tubular portion is cylindrical in shape. The second passage 216 has a generally constant diameter d2 which is approximately equal to the diameter d1 of the first tubular portion 160. Thus, the cross-sectional area of the second passage portion 216 at the second end 202 of the second tubular portion 180, which is a function of the diameter d2, is approximately the same as the cross-sectional area at the first end 200 of the second tubular portion and is approximately the same as the cross-sectional area of the first passage portion 170 in the first tubular portion 160.

In the expanded condition (FIG. 6), the guide member 230 is located in the second terminal end 224 of the arcuate slot 220 in the second tubular portion 180 and the second tubular portion has a conical configuration. At the second end 202 of the second tubular portion 180, the second passage portion 216 has a diameter d3 which is larger than the diameter d2 of the second passage portion at the first end 200. Preferably, the diameter d3 of the second passage portion 216 at the second end 202 of the second tubular portion is 40% to 90% greater than the diameter d2 of the second passage portion at the first end 200. Thus, in the expanded condition, the cross-sectional area of the second passage portion 216 at the second end 202 of the second tubular portion 180, which is function of the diameter d3, is greater than the cross-sectional area of the second passage portion at the first end 200 of the second tubular portion. Although the cross-sectional area at the second end 202 is shown as being circular in FIG. 6, it is contemplated that the cross-sectional area at the second end 202 could be any shape, such as oval shaped.

The cannula 150 includes an outer member (not shown) for maintaining the second tubular portion 180 of the cannula in the contracted condition. It is contemplated that other suitable means for maintaining the second tubular portion 180 in the contracted condition could be employed. In accordance with the present invention, the outer member may be similar to the layer 100 shown in FIG. 1 and include a section of plastic tubing which is heat shrunk over both the first and second tubular portions 160 and 180 to hold the second tubular portion in the contracted condition. In addition, a loop of polyester string (not shown) for tearing the heat shrink tubing is wrapped around the heat shrink tubing so that it extends both underneath and on top of the tubing. An outer end of the string extends beyond the tubing.

During an endoscopic surgical procedure, the cannula 150 is inserted through an incision into the body of a patient in the contracted condition. The cannula 150 is inserted through the incision using step dilation. The second tubular portion 180 is inserted inside the body. The first tubular portion 160 is inserted into the incision so that the first tubular portion extends from an exterior of the body to inside the body.

The outer end of the string is then manually pulled on by the surgeon. Pulling on the string tears the heat shrink tubing. With the heat shrink tubing torn, the second tubular portion 180 of the cannula 150 is thereby released for expansion toward the expanded condition.

Figure 11:
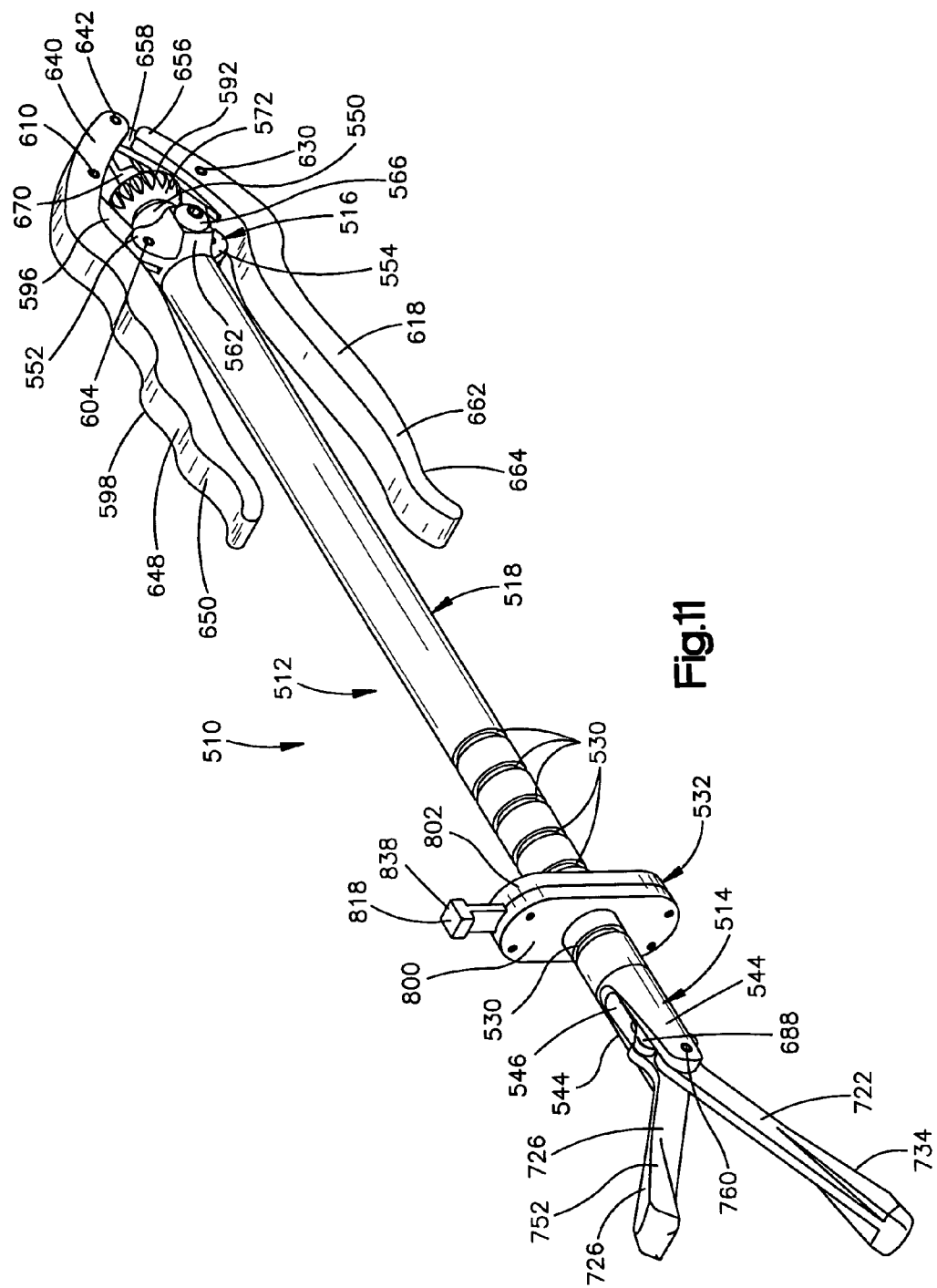
FIG. 11 is a perspective view of a surgical tool constructed in accordance with a third embodiment of the present invention.
Figure 12:
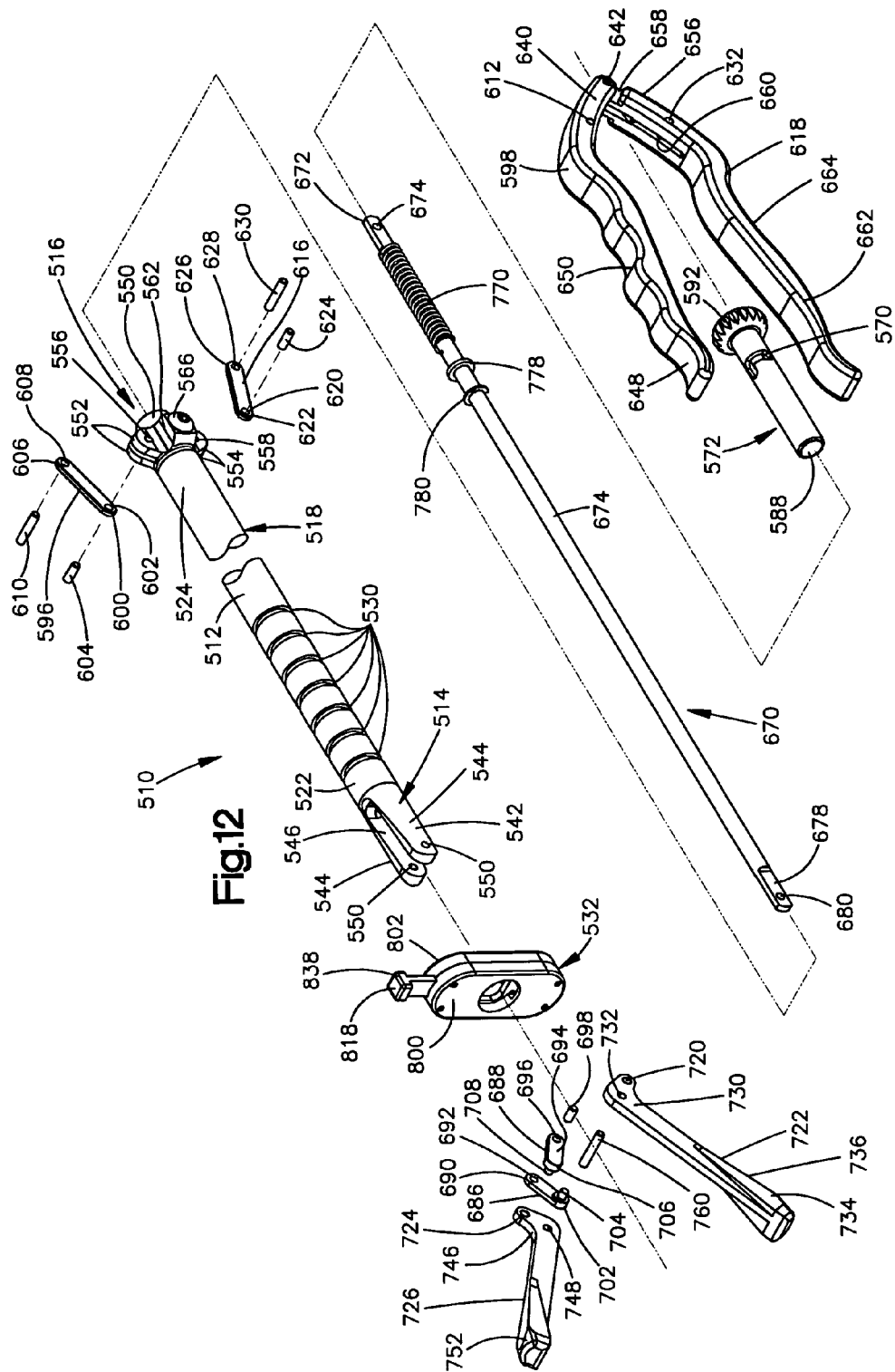
FIG. 12 is an exploded perspective view of the surgical tool of FIG. 11.

Next, one of the expansion tools 112, 410, and 510, shown in FIGS. 1, 10, and 11, is inserted into the passage 156 in the cannula 150 until the end section 118, 418, or 734 and 752 is located at the second end 202 of the second tubular portion 180. The legs 114, 414, or 722 and 726 of the expansion tool 112, 410, or 510 are manually separated, causing the frustoconical halves 118 or ends 418, or 734 and 752 to separate also. As the halves 118 or ends 418, or 734 and 752 separate, a radially outwardly directed force is exerted on the inner surface 212 of the second tubular portion 180 by the halves 118, or ends 418, or end 734 and 752, causing the second tubular portion to expand toward the expanded condition. Under the force of the expanding expansion tool 112, 410, or 510, the guide member 230 slides from the first terminal end of the arcuate slot 220 to the second terminal end of the arcuate slot to permit the expansion of the second tubular portion 180. The expansion tool 112, 410, or 510 can be rotated about the axis 154 to ensure that the second tubular portion 180 of the cannula 150 is completely expanded to the expanded condition. The expansion tool 112, 410, or 510 is then collapsed and removed so that one or more surgical instruments can be received through the cannula 150 and inserted into a patient's body.

The expandable second tubular portion 180 of the cannula 150 provides a significantly larger working area for the surgeon inside the body within the confines of the cannula. As a result, the simultaneous use of a number of endoscopic surgical instruments, including but not limited to steerable instruments, shavers, dissectors, scissors, forceps, retractors, dilators, and endoscopes, is made possible by the expandable cannula 150.

A cannula 250 constructed according to another embodiment is illustrated in FIGS. 8-9. In the embodiment of the cannula 150 illustrated in FIGS. 6-7 the tubular portions 160 and 180 are connected by a screw 206 and nut 208 and the guide member is a screw 230. In the embodiment of the cannula 250 illustrated in FIGS. 8-9 the tubular portions are connected by a rivet and the guide member is a rivet. The cannula 250 is generally similar to the cannula 150 shown in FIGS. 6-7. Accordingly, only the rivets will be described in detail.

The cannula 250 (FIG. 8) includes a tubular structure 252 centered on an axis 254. The tubular structure 252 defines a passage 256 through the cannula 250. The tubular structure 252 includes a first tubular portion 260 and a second tubular portion 280 attached to the first tubular portion. The first tubular portion 260 has a proximal end 262 and a distal end 264. Parallel cylindrical inner and outer surfaces 266 and 268 extend between the ends 262, 264 of the first tubular portion 260. The inner surface 266 defines a first passage portion 270 of the passage 256 through the cannula 250. The inner surface 266 could have a non-reflective coating (not shown).

The second tubular portion 280 (FIG. 8) of the tubular structure 252 is attached to the distal end 264 of the first tubular portion 260. The second tubular portion 280 includes an arcuate segment 282 of sheet stock. The arcuate segment 282 includes first and second arcuate edges 284 and 286. The arcuate segment 282 also includes a first planar edge 288 and a second planar edge extending between the arcuate edges 284 and 286, which is not shown in FIG. 8. The first and second planar edges are rolled in an overlapping manner to form the tubular configuration of the second tubular portion 280.

When the second tubular portion 280 has been rolled into its tubular configuration, the first and second arcuate edges 284 and 286 define oppositely disposed first and second ends 300 and 302 of the second tubular portion. The first and second ends 300 and 302 are connected by a central portion 304. The first end 300 of the second tubular portion 280 is attached to the distal end 264 of the first tubular portion 260 by a rivet 306. The rivet 306 extends through two aligned apertures 340 at the first end 300 of the second tubular portion 280. The first end 300 of the second tubular portion 280 is pivotable about the rivet 306.

The rivet 306 (FIGS. 8 and 9) has a first portion 308 and a second portion 310. The first portion 308 has a shaft 312 extending from a head 314. The shaft 312 extends through the apertures 340 in the tubular portion 280 and the head engages the inner surface 266 of the first tubular portion 260. A cylindrical opening 316 extends through the shaft 312 and the head 314.

The second portion 310 of the rivet 306 has a shaft 318 extending from a head 320. The shaft 318 extends into the opening 316 in the first portion 308 of the rivet 306 and the head 320 engages the second tubular portion 280. The shaft 318 of the second portion 310 extends into the opening 316 in the first portion 308 to connect the first and second portions of the rivet 306 and pivotally connect the second tubular portion 280 to the first tubular portion 260.

The second tubular portion 280 (FIG. 8) includes parallel inner and outer surfaces 322 and 324 extending between the first and second ends 300 and 302. The inner surface 322 defines a second passage portion 326 of the passage 256 through the cannula 250 which extends as a continuation of the first passage portion 270 in the first tubular portion 260. The inner surface 322 could have a non-reflective coating (not shown).

An arcuate slot 330 is formed in the second tubular portion 280 and extends between the inner and outer surfaces 322 and 324 of the second tubular portion. The arcuate slot 330 extends along a curvilinear path in the central portion 304 of the second tubular portion 280 toward the end 284 of the second tubular portion. The arcuate slot 330 has a first terminal end (not shown) located in the central portion 304 of the second tubular portion 280. A second terminal end 334 of the arcuate slot 330 is located adjacent the intersection of the second arcuate edge 286 and the planar edge 288 of the arcuate segment 282.

A rivet 336 is attached to the inner surface 322 of the second tubular portion 280 adjacent the intersection of the second arcuate edge 286 and the planar edge (not shown). It is contemplated that a guide pin could be used instead of the rivet 336. In the tubular configuration of the second tubular portion 280, the rivet 336 is located in the arcuate slot 330 and is movable along the curvilinear path of the arcuate slot. The rivet 336 extends through a washer 338 to retain the rivet in the arcuate slot 330.

The rivet 336 is generally similar to the rivet 306 and, therefore, will not be described in detail. The rivet 336 has a first portion 342 and a second portion 344. The first portion 342 has a shaft 346 extending from a head 348. The shaft 346 extends through the slot 330 and the head 348 engages the washer 338. A cylindrical opening 350 extends through the shaft 346 and the head 348.

The second portion 344 of the rivet 336 has a shaft 352 extending from a head 354. The shaft 352 extends into the opening 350 in the first portion 342 of the rivet 336 and the head 354 engages the outer surface 324 of the second tubular portion 280. The shaft 352 extends into the opening 350 to connect the first portion 342 of the rivet 336 to the second portion 344.

The second tubular portion 280 of the tubular structure 252 is expandable from a contracted condition to an expanded condition, shown in FIG. 8. In the contracted condition the rivet 336 is located in the first terminal end (not shown) of the arcuate slot 330 in the second tubular portion 280 and the second passage portion 326 defined by the second tubular portion is cylindrical in shape. The second passage portion 326 has a generally constant diameter which is approximately equal to the diameter of the first tubular portion 260. Thus, the cross-sectional area of the second passage portion 326 at the second end 302 of the second tubular portion 280 is approximately the same as the cross-sectional area at the first end 300 of the second tubular portion and is approximately the same as the cross-sectional area of the first passage portion 270 in the first tubular portion 260.

In the expanded condition (FIG. 8), the rivet 336 is located in the second terminal end 334 of the arcuate slot 330 in the second tubular portion 280 and the second tubular portion has a conical configuration. At the second end 302 of the second tubular portion 280, the second passage portion 326 has a diameter which is larger than the diameter of the second passage portion at the first end 300. Thus, in the expanded condition, the cross-sectional area of the second passage portion 326 at the second end 302 of the second tubular portion 280 is greater than the cross-sectional area of the second passage portion at the first end 300 of the second tubular portion. Although the cross-sectional area at the second end 302 is shown as being circular in FIG. 8, it is contemplated that the cross-sectional area at the second end 302 could be any shape, such as oval shaped.

During an endoscopic surgical procedure, the cannula 250 is inserted through an incision into the body of a patient in the contracted condition. The cannula 250 is inserted through the incision using step dilation. The second tubular portion 280 is inserted inside the body. The first tubular portion 260 is inserted into the incision so that the first tubular portion extends from an exterior of the body to inside the body.

Heat shrink tubing is torn from the cannula 250 by the surgeon. With the heat shrink tubing torn, the second tubular portion 280 of the cannula 250 is thereby released for expansion toward the expanded condition. Next, one of the expansion tools 112, 410 or 510 shown in FIGS. 1, 10, and 11 is inserted into the passage 256 in the cannula 250 until the frustoconical end section 118, or 418, or the ends 734 and 752 is located at the second end 302 of the second tubular portion 280. The legs 114, 414, or 734 and 752 of the expansion tool 112, 410, or 510 are manually separated, causing the frustoconical halves 118 or ends 418, or 734 and 752 to separate also. As the halves 118 or ends 418, or 734 and 752 separate, a radially outwardly directed force is exerted on the inner surface 312 of the second tubular portion 280 by the halves 118, or ends 418, or end 734 and 752 causing the second tubular portion to expand toward the expanded condition. Under the force of the expanding expansion tool 112, 410, or 510 the rivet 336 slides from the first terminal end of the arcuate slot 330 to the second terminal end 334 of the arcuate slot to permit the expansion of the second tubular portion 280. The expansion tool 112, 410, or 510 is then collapsed and removed so that one or more surgical instruments can be received through the cannula 250 and inserted into a patient's body.

The expandable second tubular portion 280 of the cannula 250 provides a significantly larger working area for the surgeon inside the body within the confines of the cannula. As a result, the simultaneous use of a number of endoscopic surgical instruments, including but not limited to steerable instruments, shavers, dissectors, scissors, forceps, retractors, dilators, and endoscopes, is made possible by the expandable cannula 250.

It is contemplated that the cannula 10, 150, and/or the cannula 250 described herein could be the centerpiece of an endoscopic surgical kit with the surgical tool 112 and/or 410 and/or 510 which would include an assortment of surgical instruments designed and/or selected for use with the cannula. It is also contemplated that the surgical tools 112, and/or 410, and/or 510 could be used to expand any known tubular structure or cannula such as those described in U.S. Pat. No. 6,524,320 and U.S. patent application Ser. No. 10/361,887, filed Feb. 10, 2003 in the names of Gene DiPoto et al., which are incorporated herein entirely by reference.

From the above description of the invention, those skilled in the art will perceive improvements, changes and modifications. Such improvements, changes and modifications within the skill of the art are intended to be covered by the appended claims.

Having described the invention, the following is claimed:

1. A surgical tool assembly comprising:
an expandable tubular structure having an inner surface defining a path through the tubular structure for receiving surgical instruments;
a surgical tool structured to expand the tubular structure, the surgical tool including an elongate body and a first leg having a first end engageable with the inner surface of the tubular structure and a second leg having a second end engageable with the inner surface of the tubular structure, said first and second ends being moveable away from each other to apply a radially outwardly directed force to the inner surface of the tubular structure and cause expansion of the tubular structure to increase a cross-sectional area of the path along a portion of the path; and
an actuator configured to move axially with the elongate body of the surgical tool to move said first and second legs away from each other.

2. A surgical tool assembly as set forth in claim 1, said surgical tool further including first and second handles, said first and second handles being movable toward each other to move said first and second legs away from each other.

3. A surgical tool assembly as set forth in claim 2, said handles being movable toward each other to axially move said actuator to move said first and second legs away from each other.

4. A surgical tool assembly as set forth in claim 1 further including a depth limiter for limiting the depth that said surgical tool extends into the path in the tubular structure.

5. A surgical tool assembly as set forth in claim 4 wherein said depth limiter includes a plurality of positions along said surgical tool to define a plurality of depths that said surgical tool may extend into the tubular structure.

6. A surgical tool assembly as set forth in claim 1 further including a member limiting the distance that said first and second legs move away from each other.

7. A surgical tool assembly as set forth in claim 6 wherein said member includes a plurality of positions to define a plurality of distances that said first and second legs may move away from each other.

8. A surgical tool assembly as set forth in claim 1, said surgical tool further including first and second handles being movable toward each other to pivot said first and second legs relative to each other and move said first and second ends away from each other.

9. A surgical tool assembly comprising:
an expandable tubular structure having an inner surface defining a path through the tubular structure for receiving surgical instruments;
an elongate member structured to expand the tubular structure, the elongate member having a first end and a second end and an intermediate member disposed between the first and second ends;
first and second handles connected to the first end of the elongate member, the handles configured to move radially toward and away from each other;
first and second legs connected to the second end of the elongate member, the first and second legs engageable with the inner surface of the tubular structure, the first and second legs being moveable away from each other to apply a radially outwardly directed force to the inner surface of the tubular structure; and
an actuator configured to move longitudinally to move said first and second legs away from each other.

10. A surgical tool assembly as set forth in claim 9, wherein the actuator is positioned inside said elongate member.

11. A surgical tool assembly as set forth in claim 10, wherein said first and second handles are biased away from each other and the first and second legs are biased toward each other, such that moving the first and second handles toward each other causes the first and second legs to move away from each other.

12. A surgical tool assembly as set forth in claim 11, further comprising a spring disposed around the actuator, the spring biasing the first and second handles and first and second legs.

13. A surgical tool assembly as set forth in claim 9, further including a depth limiter for limiting the depth that said surgical tool extends into the path in the tubular structure.

14. A surgical tool assembly as set forth in claim 13 wherein said depth limiter includes a plurality of positions along said surgical tool to define a plurality of depths that said surgical tool may extend into the tubular structure.

15. A surgical tool assembly comprising:
an expandable tubular structure having an inner surface defining a path through the tubular structure;
a surgical tool structured to expand the tubular structure, the surgical tool including
a shaft having first and second ends;
a handle pivotally connected to the first end of the shaft, the handle configured to move between a first, expanded, configuration and a second, contracted configuration; and
first and second jaws pivotally connected to the second end of the shaft, the first and second jaws configured to move between a first, contracted configuration and a second, expanded configuration, the first and second jaws engageable with the inner surface of the tubular structure;
wherein contracting the handle causes expansion of the first and second jaws.

16. A surgical tool assembly as set forth in claim 15, further including an actuator connected to the handle and the first and second jaws.

17. A surgical tool assembly as set forth in claim 16, the actuator configured to move longitudinally along said shaft to move said first and second jaws away from each other.

18. A surgical tool assembly as set forth in claim 17, further including a spring disposed on the actuator, the spring providing a biasing force on the handle.

19. A surgical tool assembly as set forth in claim 15, wherein said handle includes first and second handle members extending radially from the shaft.

* * * * *